(12) United States Patent
Kobayashi

(10) Patent No.: US 9,826,944 B2
(45) Date of Patent: Nov. 28, 2017

(54) RADIATION DETECTOR AND X-RAY CT APPARATUS PROVIDED THEREWITH

(71) Applicant: Hitachi, LTD., Tokyo (JP)

(72) Inventor: Hiroyuki Kobayashi, Tokyo (JP)

(73) Assignee: HITACHI, LTD., Tokyo (JP)

(*) Notice: Subject to any disclaimer, the term of this patent is extended or adjusted under 35 U.S.C. 154(b) by 4 days.

(21) Appl. No.: 14/773,562

(22) PCT Filed: Mar. 4, 2014

(86) PCT No.: PCT/JP2014/055347
§ 371 (c)(1),
(2) Date: Sep. 8, 2015

(87) PCT Pub. No.: WO2014/136734
PCT Pub. Date: Sep. 12, 2014

(65) Prior Publication Data
US 2016/0015334 A1    Jan. 21, 2016

(30) Foreign Application Priority Data
Mar. 7, 2013    (JP) ................ 2013-045147

(51) Int. Cl.
*A61B 6/03* (2006.01)
*A61B 6/06* (2006.01)
(Continued)

(52) U.S. Cl.
CPC ............. *A61B 6/06* (2013.01); *A61B 6/032* (2013.01); *A61B 6/4233* (2013.01);
(Continued)

(58) Field of Classification Search
CPC ........... A61B 6/03; A61B 6/032; A61B 6/035; A61B 6/4233; A61B 6/4291; G01T 1/20;
(Continued)

(56) References Cited

U.S. PATENT DOCUMENTS 4,560,877 A * 12/1985 Hoffman ............... G01T 1/2018
250/366
5,965,893 A * 10/1999 Tonami ................ G01T 1/1648
250/370.11
(Continued)

FOREIGN PATENT DOCUMENTS

| JP | 2004-151007 A | 5/2004 |
| JP | 2008-168110 A | 7/2008 |
| JP | 2010-223837 A | 10/2010 |

*Primary Examiner* — Thomas R Artman

(57) ABSTRACT

An X-ray detector and an X-ray CT apparatus that facilitate collimator plate arrangement are characterized by comprising radiation detection element arrays in which a plurality of radiation detection elements detecting a radiation generated from a radiation source are arranged in a first direction and a second direction orthogonal to the first direction, collimator plates that are arranged along the first direction on the radiation source side of the radiation detection element arrays to remove scattered radiations, and collimator plate support members that have grooves supporting the collimator plate and are arranged along the second direction between the radiation detection elements.

6 Claims, 9 Drawing Sheets

(51) Int. Cl.
*A61B 6/00* (2006.01)
*G01T 1/29* (2006.01)
*G21K 1/02* (2006.01)

(52) U.S. Cl.
CPC .......... *A61B 6/4266* (2013.01); *A61B 6/4291* (2013.01); *A61B 6/4435* (2013.01); *A61B 6/461* (2013.01); *G01T 1/2985* (2013.01); *A61B 6/5205* (2013.01); *G21K 1/025* (2013.01)

(58) Field of Classification Search
CPC ... G01T 1/2002; G01T 1/2006; G01T 1/2018; G01T 1/24; G01T 1/244; G01T 1/2928; G01T 1/2971; G21K 1/02; G21K 1/025; G01N 23/046
See application file for complete search history.

(56) References Cited

U.S. PATENT DOCUMENTS

| | | | |
|---|---|---|---|
| 5,991,357 A * | 11/1999 | Marcovici | A61B 6/035 250/370.09 |
| 6,181,767 B1 * | 1/2001 | Harootian | A61B 6/4291 378/154 |
| 6,587,538 B2 * | 7/2003 | Igarashi | A61B 6/06 250/367 |
| 7,356,124 B2 * | 4/2008 | Freund | G01N 23/046 378/147 |
| 8,817,946 B2 * | 8/2014 | Kobayashi | A61B 6/032 250/366 |
| 8,873,705 B2 * | 10/2014 | Konno | A61B 6/032 378/19 |
| 2002/0064252 A1 * | 5/2002 | Igarashi | A61B 6/06 378/19 |
| 2006/0291617 A1 * | 12/2006 | Freund | G01N 23/046 378/19 |
| 2008/0101542 A1 * | 5/2008 | Ikhlef | G21K 1/025 378/147 |
| 2011/0129069 A1 * | 6/2011 | Freund | G21K 1/025 378/147 |
| 2012/0093280 A1 * | 4/2012 | Konno | A61B 6/032 378/7 |
| 2014/0158543 A1 * | 6/2014 | Chen | C25D 1/02 205/50 |
| 2016/0015334 A1 * | 1/2016 | Kobayashi | A61B 6/06 378/4 |

* cited by examiner

RADIATION DETECTOR AND X-RAY CT APPARATUS PROVIDED THEREWITH

TECHNICAL FIELD

The present invention relates to a radiation detector detecting an X-ray, y-ray, etc., and particular to a support member supporting a collimator plate to be provided on the radiation source side of the radiation detector in order to remove scattered radiations. The present invention relates also to an X-ray Ct apparatus provided with such a radiation detector.

BACKGROUND ART

An X-ray CT (Computed Tomography) apparatus that is one of medical image diagnostic apparatuses reconstructs a tomographic image of an object using projection data from multiple angles that can be obtained by rotating an X-ray tube device irradiating an X-ray to the object and an X-ray detector detecting distribution of the X-ray dose transmitted through the object as the projection data around the object to display the reconstructed tomographic image. The image to be displayed on the X-ray CT apparatus draws organ shapes inside the object and is used for image diagnosis.

As a radiation detector represented by an X-ray detector used for an X-ray CT apparatus, an indirect-conversion-type detector, which is provided with a detection element in which a phosphor element such as a ceramic scintillator and a light detecting element such as a photodiode are combined, is used mainly. Also, a direct-conversion-type detector, which is provided with a semiconductor element as a detection element, has been recently used. In either type of the radiation detector, a structure in which approximately one thousands of detection element s are arranged on an arc around an X-ray focus in the rotation plane and a plurality of the detection element arrays are further arranged in the rotation axis direction is adopted. Also, a number of collimator plates are provided along the rotation axis direction on the X-ray tube device side of the X-ray detector in order to remove a scattered X-ray from an X-ray transmitted through an object. The collimator plates are made of thin metal plates that can shield an X-ray sufficiently and arranged radially toward the X-ray focus.

In a modern X-ray CT apparatus, it is promoted that the rotation speed and the number of detection element arrays are increased mainly in order to shorten an examination time. Increasing the rotation speed increases a centrifugal force applied to a collimator plate, and increasing the number of detection element arrays extends a length of a collimator plate in the rotation axis direction, which results in reducing the collimator plate strength. Therefore, as the rotation speed and the number of detection element arrays are increased, a collimator plate can be easily deformed during CT scanning. The deformed collimator plate changes an amount of X-ray incident on a detection element, which causes artifact generation on a tomographic image. The patent literature 1 discloses an X-ray detector capable of reducing the collimator plate deformation and an X-ray CT apparatus therewith.

CITATION LIST

Patent Literature

PTL 1: International Patent No. 2011/074470

SUMMARY OF INVENTION

Technical Problem

In PTL 1, there is a groove provided on a resin support plate disposed parallel to an X-ray incident plane of an X-ray detector, and one end of a collimator plate is connected by engaging it in the groove provided along the rotation axis direction. In such a structure, as the number of the detection element arrays increases, the collimator plate and the groove extend the lengths in the rotation axis direction, which makes it difficult to engage the collimator plate in the groove.

Therefore, the purpose of the present invention is to provide a radiation detector and an X-ray CT apparatus in which collimator plates can be easily arranged.

Solution to Problem

In order to achieve the above purpose, the present invention is characterized by comprising radiation detection element arrays in which a plurality of radiation detection elements detecting a radiation generated from a radiation source are arranged in a first direction and a second direction orthogonal to the first direction, collimator plates arranged along the first direction on the radiation source side of the radiation detection element arrays to remove scattered radiations, and collimator plate support members that have grooves supporting the collimator plate and are arranged along the second direction between the radiation detection elements.

Advantageous Effects of Invention

According to the present invention, it can provide a radiation detector and an X-ray CT apparatus in which collimator plates can be easily arranged.

DESCRIPTION OF EMBODIMENTS

The radiation detector related to the present embodiment is characterized by comprising radiation detection element arrays in which a plurality of radiation detection elements detecting a radiation generated from a radiation source are arranged in a first direction and a second direction orthogonal to the first direction, collimator plates arranged along the first direction on the radiation source side of the radiation detection element arrays to remove scattered radiations, and collimator plate support members that have grooves supporting the collimator plate and are arranged along the second direction between the radiation detection elements.

Also, there are even numbers of the collimator plate support members, and they are characterized by being provided in symmetric positions on the basis of the central position in the first direction.

Also, a width between radiation detection elements where the collimator plate support members are arranged is characterized by being wider than a width between radiation detection elements where the collimator plate support members are not arranged.

Also, the radiation detection elements are characterized by that they are composed of scintillator elements for generating a visible light when a radiation is incident as well as light detection elements for outputting an electrical signal when the visible light is incident, that reflectors for reflecting the visible light are provided between scintillator elements, and that the collimator plate support members are composed of the same material as the reflectors.

Also, the X-ray CT apparatus related to the present embodiment is characterized by comprising the radiation source, the described radiation detector disposed opposite to the radiation source to detect a radiation transmitted through an object, a rotating disk equipped with the radiation source and the radiation detector and rotating around the object, an image reconstruction device for reconstructing a tomographic image of the object based on a transmitted radiation amount detected by the radiation detector from multiple angles, and an image display device for displaying the tomographic image reconstructed by the image reconstruction device.

Also, a position where collimator plate support members of the radiation detector are arranged is characterized by being a joint position of a maximum slice thickness during image reconstruction.

Hereinafter, the radiation detector and the X-ray CT apparatus of the present invention will be described in detail using the diagrams. Additionally, the repeated explanations of the components with the same functions are omitted by providing the same symbols in the following descriptions and the attached diagrams. Also, in order to help find a direction of each diagram, the XYZ coordinate system is shown in the lower left of each diagram.

(First Embodiment)

Figure 1:
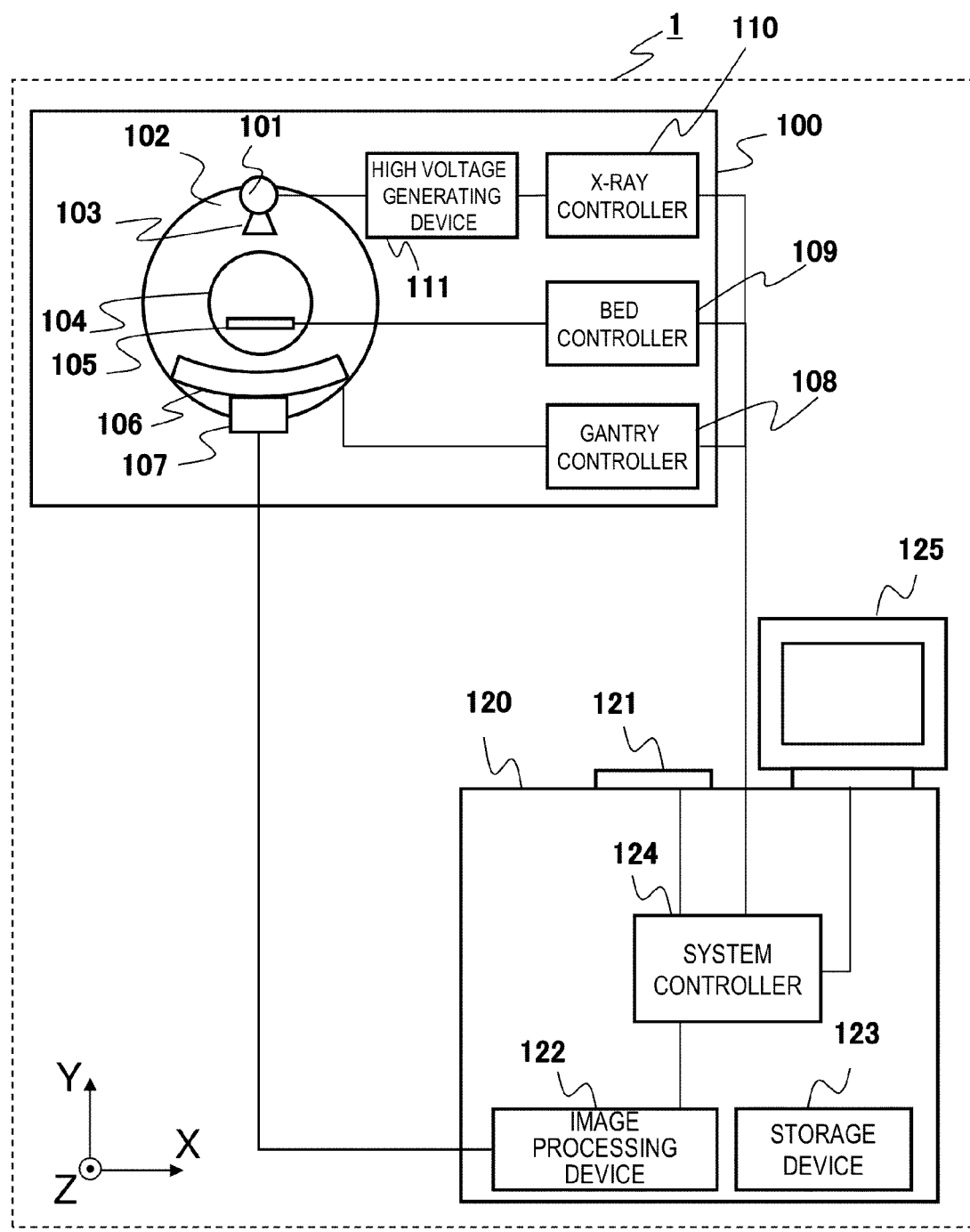
FIG. 1 is a block diagram showing the overall configuration of the X-ray CT apparatus 1 of the present invention.

First, the overall configuration of the X-ray CT apparatus of the present invention that is an example of medical image diagnostic apparatuses will be described using FIG. 1. FIG. 1 is a block diagram showing the overall configuration of the X-ray CT apparatus 1. As shown in FIG. 1, the X-ray CT apparatus 1 comprises the scan gantry unit 100 and the operation unit 120.

The scan gantry unit 100 comprises the X-ray tube device 101, the rotating disk 102, the collimator 103, the X-ray detector 106, the data collection device 107, the bed device 105, the gantry controller 108, the bed controller 109, the X-ray controller 110, and the high voltage generating device 111.

The X-ray tube device 101 is a device for irradiating an X-ray to an object placed on the bed device 105. The collimator 103 is a device for restricting a radiation range of an X-ray irradiated from the X-ray tube device 101. The rotating disk 102 is equipped with the X-ray tube device 101 and the X-ray detector 106, comprises the opening 104 for accommodating the object placed on the bed device 105, and rotates around the object.

The X-ray detector 106 is a device for measuring spatial distribution of transmitted X-rays by detecting an X-ray transmitted through an object placed opposite to the X-ray tube device 101, in which many X-ray detection elements are arranged in two dimensions of the circumferential direction in the rotation plane (XY plane) of the rotating disk 102 and the rotation axis direction (parallel to the Z axis). Additionally, the details of the X-ray detector 106 will be described later.

The data collection device 107 is a device for collecting an X-ray amount detected by the X-ray detector 106 as digital data. The gantry controller 108 is a device for controlling the rotation of the rotating disk 102. The bed controller 109 is a device for controlling up, down, left, right, back, and forth movements of the bed device 105. The high voltage generating device 111 is a device for generating a high voltage to be applied to the X-ray tube device 101. The X-ray controller 110 is a device for controlling the output of the high voltage generating device 111.

The operation console 120 comprises the input device 121, the image calculation device 122, the display device 125, the storage device 123, and the system controller 124. The input device 121 is a device for inputting an object name, an examination date, scanning conditions, etc. and is specifically a keyboard or a pointing device. The image calculation device 122 is a device for performing a calculation process for measurement data sent from the data collection device 107 to reconstruct a CT image. The display device 125 is a device for displaying a CT image generated by the image calculation device 122 and is specifically a CRT (Cathode-Ray Tube), a liquid crystal display, or the like. The storage device 123 is a device for storing data collected by the data collection device 107 and image data of the CT image generated by the image calculation device 122 and is specifically an HDD (Hard Disk Drive) or the like. The system controller 124 is a device for controlling these devices, the gantry controller 108, the bed controller 109, and the X-ray controller 110.

The X-ray controller 110 controls the high voltage generating device 111 based on scanning conditions input from the input device 121, such as a tube voltage and a tube current particularly, which supplies predetermined electric power from the high voltage generating device 111 to the X-ray tube device 101. The X-ray tube device 101 irradiates an X-ray according to the scanning conditions to an object using the supplied electric power. The X-ray detector 106 detects an X-ray irradiated from the X-ray tube device 101 and transmitted through the object using many X-ray detection elements to measure distribution of the transmitted X-ray. The rotating disk 102 is controlled by the gantry controller 108 and rotates based on scanning conditions input from the input device 121, such as a rotation speed particularly. The bed device 105 is controlled by the bed controller 109 and operates based on scanning conditions input from the input device 121, such as a helical pitch particularly.

By repeating an X-ray irradiation from the X-ray tube device 101 and a measurement of distribution of transmitted X-rays using the X-ray detector 106 together with rotation of the rotating disk 102, projection data from various angles are acquired. The projected data is associated with a view that shows each angle and a channel (ch) number as well as an array number that are detection element numbers of the X-ray detector 106. The acquired projection data from various angles is transmitted to the image processing device 122. The image processing device 122 performs a back projection process for the transmitted projection data from various angles to reconstruct a CT image. The CT image acquired by the reconstruction is displayed on the display device 125.

Figure 2:
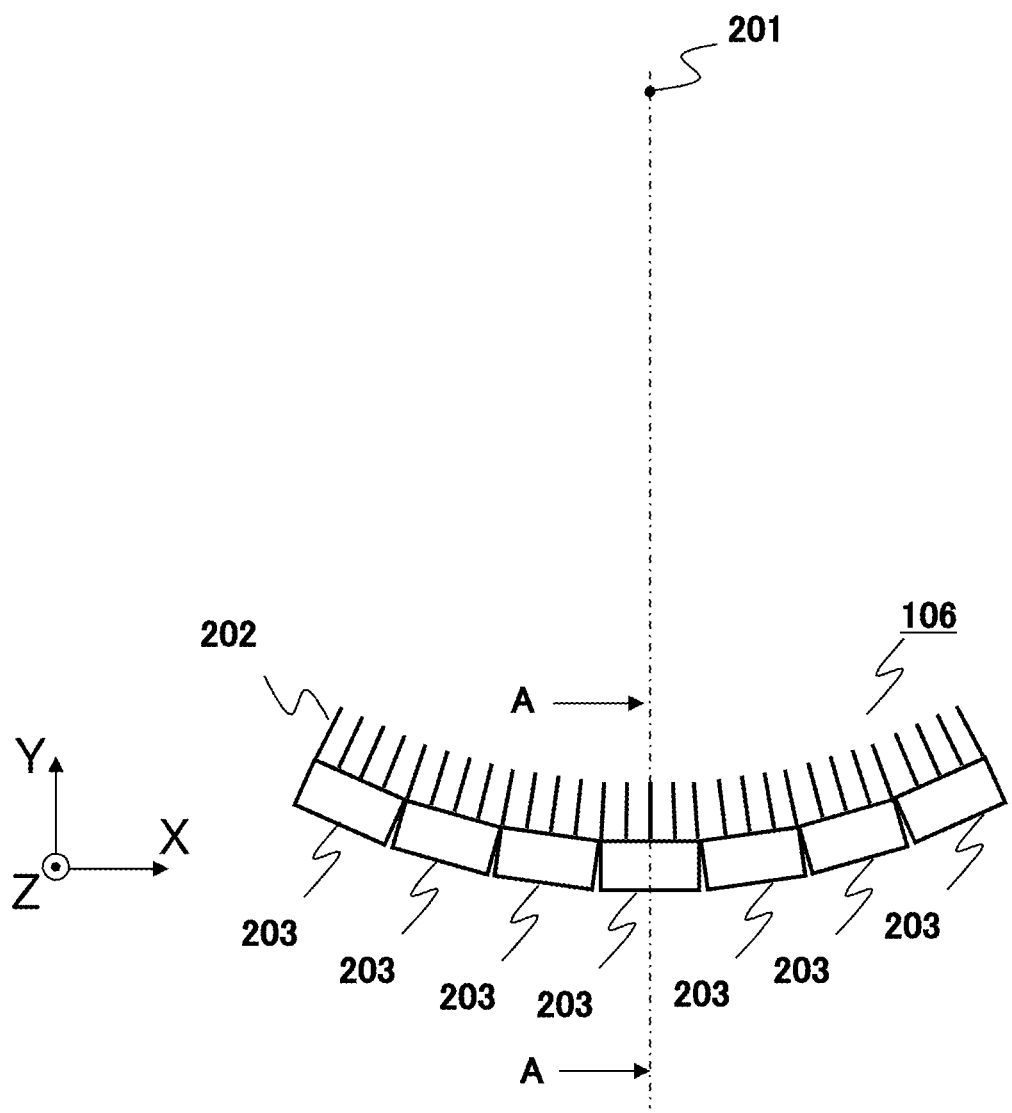
FIG. 2 is a diagram explaining the positional relationship between the X-ray focus 201 and the X-ray detector 106.

The X-ray detector 106 will be described using FIG. 2. FIG. 2 is a diagram showing the positional relationship between the X-ray focus 201 and the X-ray detector 106. The X-ray detector 106 comprises the scattered radiation remover 202 and the detection element modules 203.

The scattered radiation remover 202 removes scattered radiations generated by an object or the like and is configured so that the metal thin plates which can sufficiently shield an X-ray are disposed radially toward the X-ray focus 201 as described later. When an X-ray including scattered radiations is detected by the X-ray detector 106, an X-ray amount reduced by the object is not measured properly, which deteriorates the image quality of the reconstructed tomographic image.

The detection element modules 203 measures spatial distribution of an X-ray transmitted through the scattered radiation remover 202 and configured so that X-ray detection elements measuring an X-ray amount are arranged on a flat plate two-dimensionally. The X-ray detector 106 is provided with a plurality of the detection element modules 203, and the respective detection element modules 203 are arranged so as to be a polygonal shape formed by tangent lines of the arc around the X-ray focus 201 on the rotating plane (XY plane) of the rotating disk 102. By thus arranging the respective detection element modules 203, X-ray detection elements are almost arranged on the arc around the X-ray focus 201. Additionally, although the only seven detection element modules 203 are drawn in FIG. 2 in order to simplify the diagram, the number of the detection element modules 203 is not limited to seven.

Figure 3:
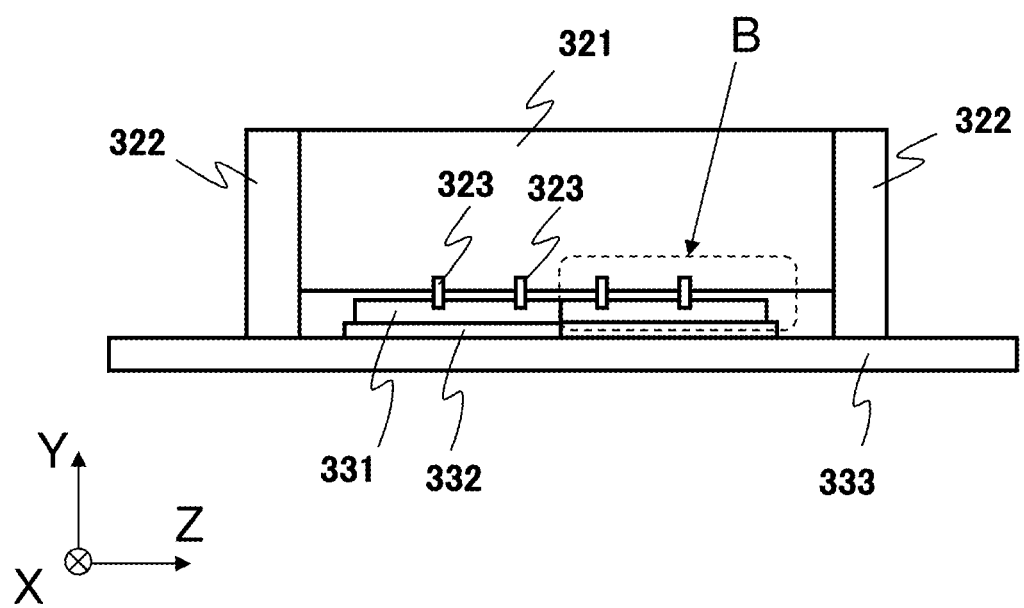
FIG. 3 is a diagram showing the configuration of the first embodiment and the A-A cross-sectional diagram of FIG. 2.
Figure 4:
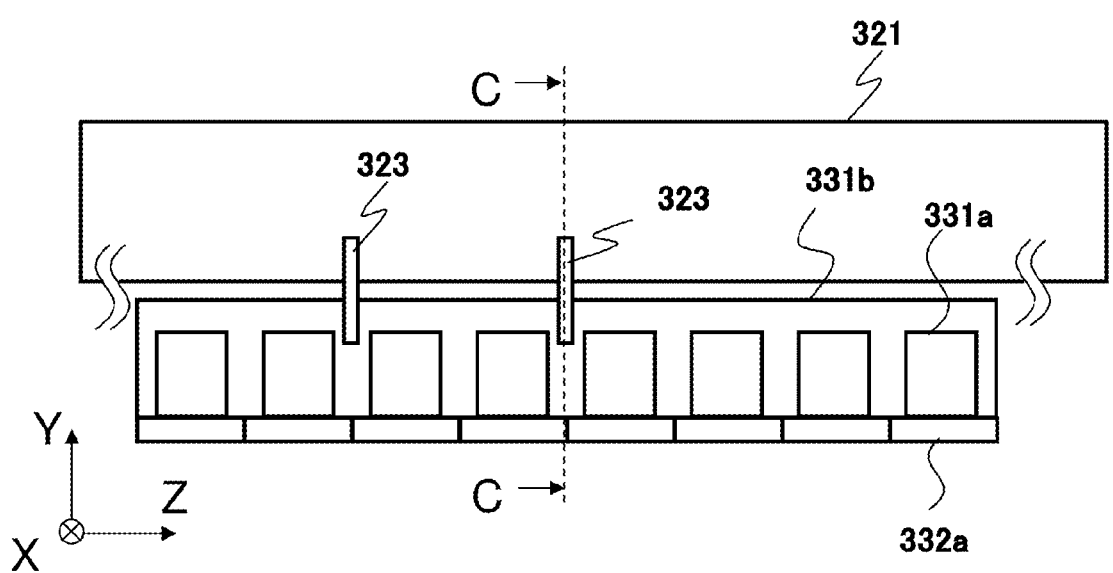
FIG. 4 is a diagram showing the main part of the first embodiment and the enlarged view in B of FIG. 3.
Figure 5:
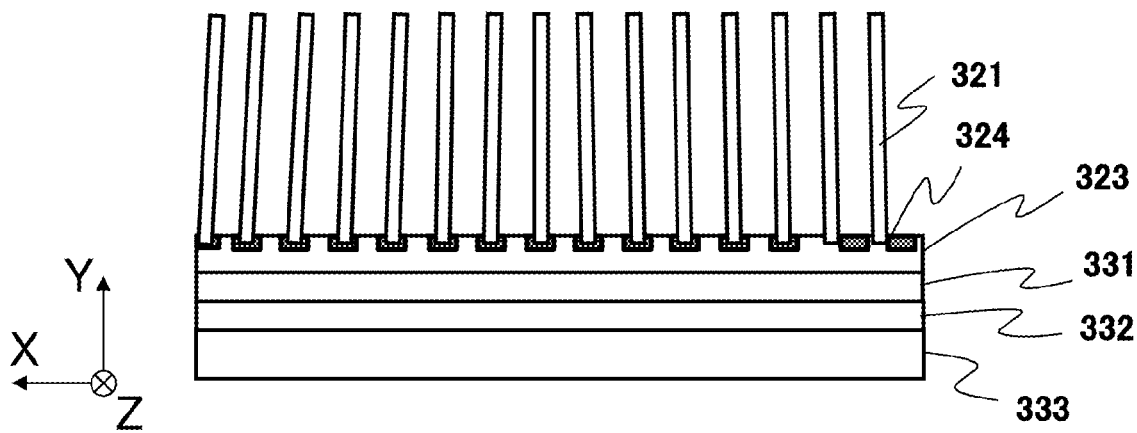
FIG. 5 is a diagram showing the main part of the first embodiment and the C-C cross-sectional diagram of FIG. 4.

The scattered radiation remover 202 and the detection element modules 203 will be described using FIGS. 3 to 5. FIG. 3 is the A-A cross-sectional diagram in FIG. 2, and the left and right direction is the rotation direction (parallel to the Z axis) of the rotating disk 102. FIG. 4 is the enlarged view in B of FIG. 3. FIG. 5 is the C-C cross-sectional diagram in FIG. 4, and the direction perpendicular to a plane where the diagram is drawn is the rotation axis direction (parallel to the Z axis) of the rotating disk 102.

The detection element module 203 comprises the substrate 333, the light detection element array 332, and the scintillator element array 331. The scattered radiation remover 202 comprises the collimator plate 321, the grooved pillar 322, and the collimator plate support members 323.

The substrate 333 holds the light detection element array 332 and the grooved pillar 322 and is made of glass epoxy or the like.

The light detection element array 332 is installed on the upper plane of the substrate 333, on which the light detection elements 332a detecting light emission of the scintillator element array 331 are arranged two-dimensionally. For example, a photodiode is used for the light detection elements 332a.

The scintillator element array 331 is installed on the upper plane of the light detection element array 332, on which the scintillator elements 331a emitting visible lights in an amount according to the X-ray amount by receiving an X-ray light are partitioned with the light reflectors 331b and arranged two-dimensionally. The scintillator elements 331 and the light detection elements 332a are respectively associated as a pair, and one X-ray detection element is composed of a pair of the scintillator element 331 and the light detection element 332a. The light reflector 331b reflects a visible light emitted by the scintillator element 331a and is formed by fixing white powder such as titanium oxide with a transparent adhesive such as epoxy resin. The thicker the thickness of the light reflector 331b is or the denser the concentration of the white powder in the light reflector 331b is, the more the leakage of a visible light to an adjacent X-ray detection element can be reduced.

As the number of X-ray detection elements to be arrayed is increased for the light detection element array 332 and the scintillator element array 331, the yield rate of the components is reduced, or the assembly difficulty is increased. Therefore, in order to avoid these problems, the number of the X-ray detection elements to be arrayed may be increased by dividing and combining at least one of the light detection element array 332, the scintillator element array 331, and the substrate 333. FIG. 3 shows a configuration example where the light detection element array 332 and the scintillator element array 331 are respectively divided into two in the rotation axis direction and combined on one substrate 333. The division mode is not limited to FIG. 3.

The collimator plate 321 is a thin metal plate that can shield an X-ray sufficiently and is formed with a plate member of a heavy metal such as tungsten and molybdenum. The collimator plates 321 are arranged so that shadows formed by the collimator plates 321 when the X-ray detector 106 is viewed from the X-ray focus 201 locate along the rotation axis direction (parallel to the Z axis between X-ray detection elements almost arranged on an arc. Specifically, the collimator plates 321 are arranged radially toward the X-ray focus 201 on the rotating plane (XY plane) of the rotating disk 102 or parallel to the rotation axis direction (parallel to the Z axis). By thus arranging the collimator plates 321, direct radiations from the X-ray focus 201 are incident on the X-ray detection elements, scattered radiations generated by an object shielded are shielded by the collimator plates 321, which prevents from being incident on the X-ray detection elements.

The grooved pillars 322 support the collimator plate 321 at the end of the rotation axis direction (parallel to the Z axis), have grooves on the sides that are not shown in the diagram, and are installed on the substrate 333. The grooves of the grooved pillars 322 are formed radially toward the X-ray focus 201 in the rotation plane (XY plane). By inserting the collimator plate 321 in the grooves of the grooved pillars 322, the collimator plates 321 are arranged radially toward the X-ray focus 201 in the rotation plane (XY plane). The collimator plate 321 and the grooved pillars 322 may be fixed by an adhesive.

The collimator plate support members 323 support the collimator plate 321 from the X-ray detector 106 side and is installed on the scintillator element array 331. The collimator plate support members 323 are arranged between X-ray detection elements aligned along the rotation axis direction (parallel to the Z axis) and have the grooves 324 to insert the collimator plates 321. The grooves 324 are formed between the X-ray detection elements almost aligned on an arc in the rotation plane (XY plane). The shape of the groove 324 may not be limited unless the shape does not hinder the collimator plates 321 to be inserted from being arranged radially toward the X-ray focus 201. Also, the collimator plate 321 inserted in the grooves 324 may be fixed by an adhesive.

The thickness of the collimator plate support member 323 is formed thinner than a gap between X-ray detection elements aligned along the rotation axis direction so that the collimator plate support member 323 does not come into contact with the scintillator element 331a forming an X-ray detection element. In order to reduce absorption of an X-ray by the collimator plate support members 323, it is desirable that the material of the collimator plate support members 323 is, for example, an epoxy resin or the like whose X-ray absorption rate is low. Also, in order to reduce an amount of which the collimator plate support members 323 absorb a visible light generated from the scintillator element 331a, it is desirable that the material of the collimator plate support members 323 is the same as that of the light reflector 331b.

Although the collimator plate support members 323 may be arranged in any positions between X-ray detection elements aligned along the rotation axis direction, the collimator plate support members 323 should be desirably arranged in symmetrical positions based on the central position of the X-ray detector in the rotation axis direction. The collimator plate support members 323 are arranged in symmetrical positions in the rotation axis direction, which can support the collimator plates 321 more uniformly.

Additionally, the collimator plate support members 323 are arranged desirably in joint positions of the maximum slice thickness in the rotation axis direction during image reconstruction. A multi-slice detector in which a plurality of X-ray detection element arrays are aligned in the rotation axis direction can reconstruct an image for each X-ray detection element array as well as acquire an image with a thick slice by adding plural arrays of measurement data. For example, a 64-array multi-slice detector can acquire 64 images in one measurement as well as acquire four images at a 16-time thickness by adding 16 arrays of measurement data. By the way, if there is a foreign substance like the collimator plate support member 323 in a slice thickness, the image quality of the image with the said slice thickness can be deteriorated.

Figure 6:
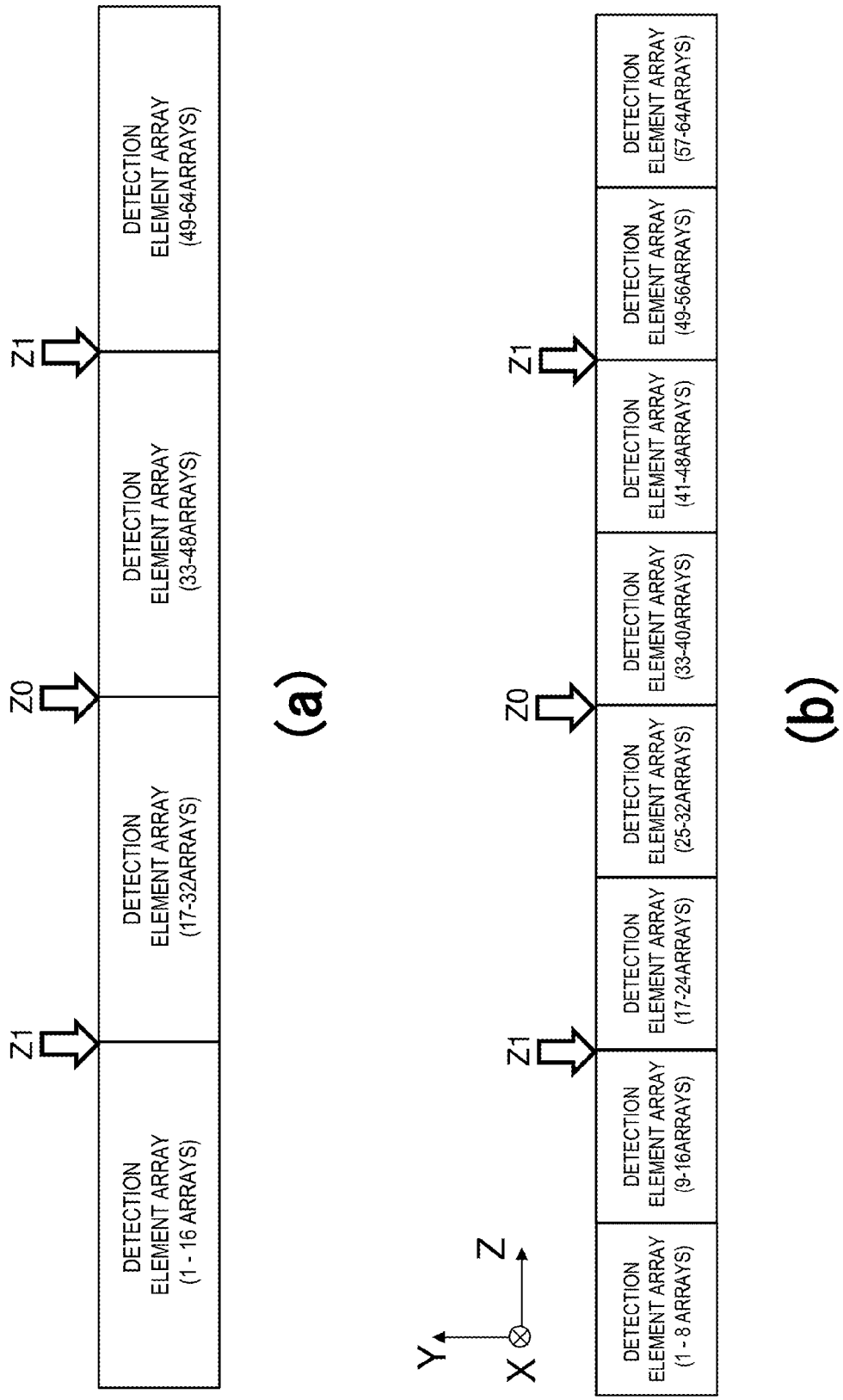
FIG. 6 is a diagram showing an example of positions where the collimator plate support members 323 are arranged.

Therefore, in order to prevent such image quality deterioration, it is desirable that the collimator plate support members 323 are arranged in joint positions of the maximum slice thickness during image reconstruction. A specific arrangement example will be described using FIG. 6. FIG. 6 is the schematic diagram of the 64-array multi-slice detector, FIG. 6(a) shows a case of adding 16 arrays of measurement data, and FIG. 6(b) shows a case of adding 8 arrays of measurement data. In a case of forming the maximum slice thickness by 16 arrays in the multi-slice detector of FIG. 6, the Z0 and Z1 positions in the diagram are joint positions of the maximum slice thickness. If the collimator plate support members 323 are arranged in these positions, the collimator plate support members 323 do not exist in a said slice thickness whatever the thickness is.

That is, not only when adding 16 arrays of measurement data shown in FIG. 6(a), but also when adding 8 arrays of measurement data shown in FIG. 6(b), or even when adding 4 or 2 arrays of measurement data that is not shown in the diagram, there is no foreign substance like the collimator plate support member 323 in a slice thickness, which can prevent image quality deterioration.

Additionally, it may be configured so that the collimator plate support members 323 are arranged out of the center position of the X-ray detector in the rotation axis direction. The center position of the X-ray detector in the rotation axis direction, i.e. the Z0 position in FIG. 6 is a position where a high-quality tomographic image is easily acquired because an X-ray incident on the X-ray detection element is approximately orthogonal to the incident plane. If there is a foreign substance like the collimator plate support member 323 in such a position, the image quality of the high-quality tomographic image can be deteriorated.

Therefore, it may be configured so that the collimator plate support members 323 are arranged out of the center position of the X-ray detector in the rotation axis direction. By thus arranging the collimator plate support members 323, the image quality deterioration in a position where a high-quality tomographic image is easily acquired can be prevented.

According to the configuration described above, even if the number of detection element arrays increases, the collimator plates 321 can be easily inserted in the grooves 324 of the collimator plate support members 323, which can provide a radiation detector facilitating arrangement of the collimator plates 321 as well as an X-ray CT apparatus equipped with such a radiation detector.

Also, by selecting a material of the collimator plate support member 323 properly, output reduction of the X-ray detector due to the collimator plate support members 323 can be reduced. Additionally, image quality deterioration can be prevented by arranging the collimator plate support members 323 in appropriate positions.

(Second Embodiment)

Figure 7:
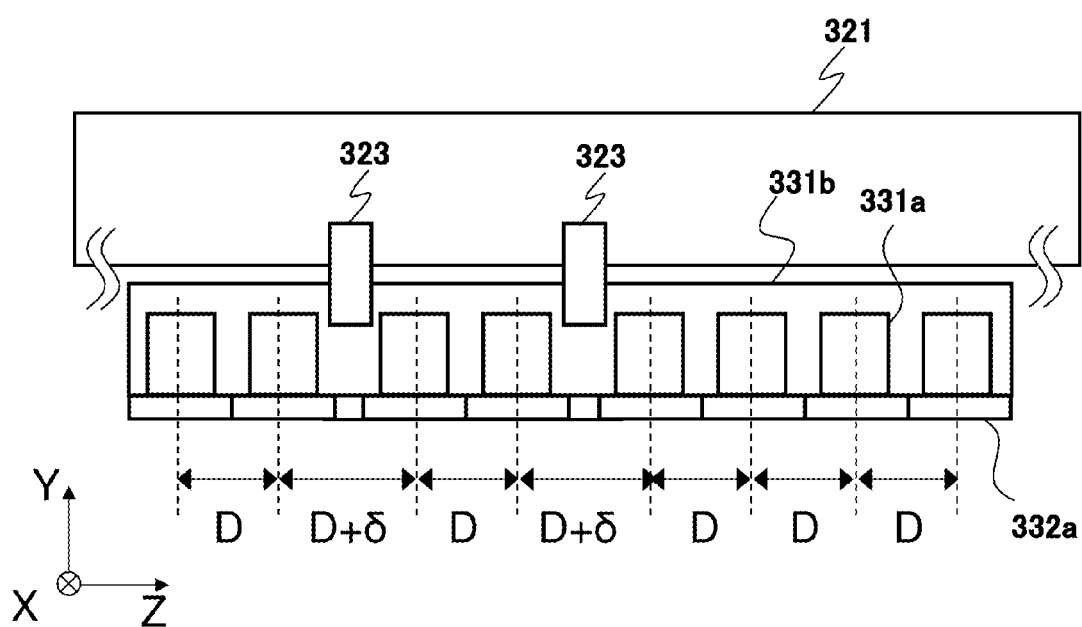
FIG. 7 is a diagram showing the main part of the second embodiment.

The second embodiment will be described using FIG. 7. The point different from the first embodiment is that X-ray detection elements have irregular gaps partly in the rotation axis direction (parallel to the Z axis), and the same descriptions will be omitted because the others are the same as the first embodiment. Additionally, FIG. 7 can be substituted for FIG. 4 of the first embodiment.

Depending on the material and the number of the collimator plate support members 323, there is a case of lacking the mechanical strength of the collimator plate support members 323 formed thinner than gaps between X-ray detection elements aligned along the rotation axis direction to support the collimator plates 321. In order to supplement the insufficient mechanical strength of the collimator plate support members 323, the thickness of the collimator plate support members 323 should be increased. However, if the collimator plate support members 323 are thicker than the gaps between the X-ray detection elements aligned along the rotation axis direction, the collimator plate support members 323 interfere with the X-ray detection elements, which results in lowering output signals of the X-ray detection elements adjacent to the collimator plate support members 323.

Therefore, in the present embodiment, the widths between the X-ray detection elements where the collimator plate support members 323 are arranged are made wider than those between the X-ray detection elements where the collimator plate support members 323 are not arranged so that the collimator plate support members 323 do not interfere with the X-ray detection elements even when the thickness of the collimator plate support members 323 is increased to supplement the insufficient mechanical strength. Specifically, as shown in FIG. 7, the widths between the X-ray detection elements where the collimator plate support members 323 are arranged are expressed as $D+\delta$ ($\delta \neq 0$) while the widths between the X-ray detection elements where the collimator plate support members 323 are not arranged are expressed as D. Additionally, in case of such a configuration, because the X-ray detection elements have irregular gaps partly in the rotation axis direction, the image calculation device 122 performs a process to correct a positional shift in the rotation axis direction for measurement data sent from the data collection device 107 before an inverse projection process is performed.

According to the configuration described above, even if the number of detection element arrays increases, the collimator plates 321 can be easily inserted in the grooves 324 of the collimator plate support members 323, which can provide a radiation detector facilitating arrangement of the collimator plates 321 as well as an X-ray CT apparatus equipped with such a radiation detector. Additionally, the radiation detector can be configured without causing insufficient mechanical strength of the collimator plate support members 323.

(Third Embodiment)

Figure 8:
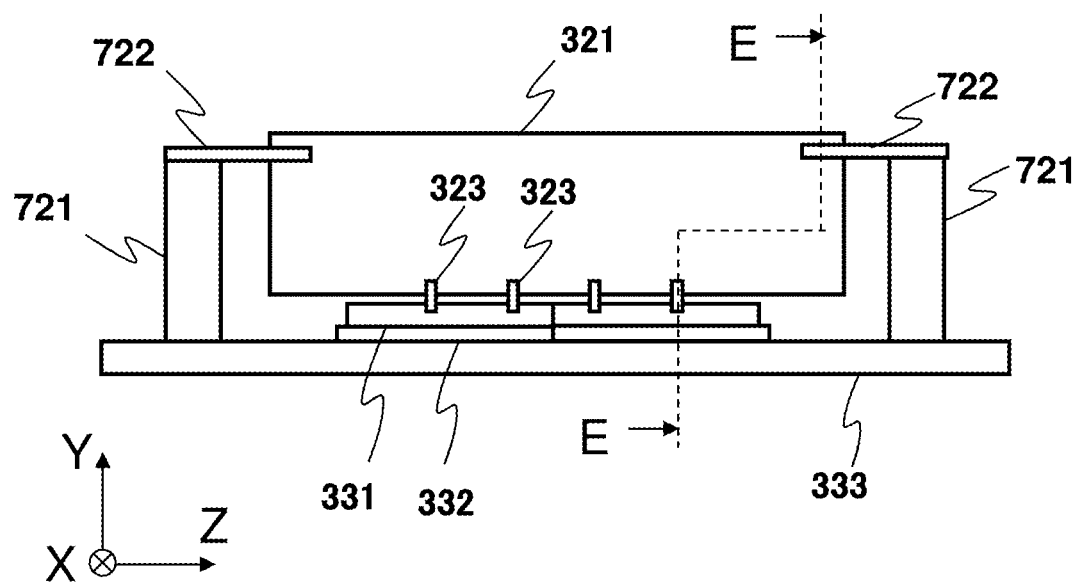
FIG. 8 is a diagram showing the configuration of the third embodiment and the A-A cross-sectional diagram of FIG. 2.
Figure 9:
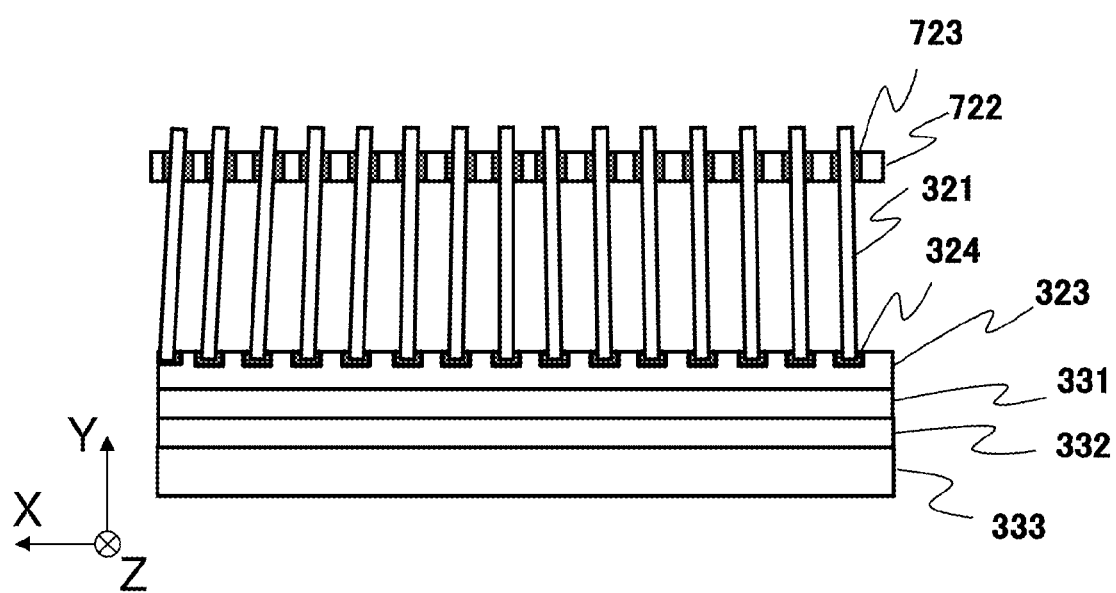
FIG. 9 is a diagram showing the main part of the third embodiment and the E-E cross-sectional diagram of FIG. 7.

The third embodiment will be described using FIGS. 8 and 9. The point different from the first embodiment is that the pillars 721 and the grooved flat plates 722 are used instead of the grooved pillars 322, and the same descriptions will be omitted because the others are the same as the first embodiment. Additionally, FIG. 8 can be substituted for FIG. 3 of the first embodiment. Also, FIG. 9 is the E-E cross-sectional diagram in FIG. 8 and can be substituted for FIG. 5 of the first embodiment.

The pillars 721 support the grooved flat plates 722 and are installed on the substrate 333. The height of the pillars 721 is lower than the height of which the light detection element array 332, the scintillator element array 331, the collimator plate support members 323, and the collimator plate 321 are assembled.

The grooved flat plates 722 support the collimator plate 321 from the rotation axis direction and are installed on the upper ends of the pillars 721. The grooved flat plate 722 has the groove 723 to insert the collimator plate 321, and the position of the groove 723 is between X-ray detection elements in the rotation plane (XY plane). The gap between the respective grooves 723 is slightly narrower than that between the grooves 324 provided for the collimator plate support members 323, and the grooves 723 as well as the grooves 324 are provided so that the collimator plates 321 are arranged radially toward the X-ray focus 201. The shape of the groove 723 may not be limited unless the shape does not hinder the collimator plates 321 from being arranged radially toward the X-ray focus 201. Also, the collimator plate 321 inserted in the grooves 723 may be fixed by an adhesive.

In case of the grooved flat plates 722 having such a structure, a groove process can be simultaneously performed for a plurality of accumulated flat plates, which can reduce the processing cost. Also, in the directions between the X-ray focus 201 and the respective detection elements, the length of the groove 723 of the grooved flat plate 722 is shorter than that of the groove of the grooved pillar 322 in the first embodiment, which can insert the collimator plate 321 easily.

According to the configuration described above, even if the number of detection element arrays increases, the collimator plates 321 can be easily inserted in the grooves 324 of the collimator plate support members 323, which can provide a radiation detector facilitating arrangement of the collimator plates 321 as well as an X-ray CT apparatus equipped with such a radiation detector. Additionally, the collimator plates 321 can be easily inserted in the grooves 723 of the grooved flat plate 722.

Additionally, the embodiments described above are not for limiting the structure of the present invention but examples showing specific embodiments, and the present invention can be achieved even in the other embodiments having the same effect. For example, although an indirect conversion type of detector in which the scintillator element array 331 and the light detection element array 332 are combined are described in the above embodiments, the present invention can be achieved also by a direct conversion type of detector in which the combination of the scintillator element array 331 and the light detection element array 332 is replaced with a semiconductor element array.

Also, although the embodiments are described by taking an X-ray detector as an example, the present invention also includes a radiation detector such as a detector detecting a y ray. Also, although an X-ray tube device is described as an example of a radiation source, a y ray generating source using an isotope may be used.

DESCRIPTION OF REFERENCE NUMERALS

1: X-ray CT apparatus
100: scan gantry unit
101: X-ray tube device
102: rotating disk
103: collimator
104: opening
105: bed device
106: X-ray detector
107: data collection device
108: gantry controller
109: bed controller
110: X-ray controller
111: high voltage generating device
120: operation console
121: input device
122: image calculation device
123: storage device
124: system controller
125: display device
201: X-ray focus
202: scattered radiation remover
203: detection element module
321: collimator plate
322: grooved pillar
323: collimator plate support member
324: groove
331: scintillator element array
331a: scintillator element
331b: light reflector
332: light detection element array
332a: light detection element
333: substrate
721: pillar
722: grooved flat plate
723: groove

The invention claimed is:

1. A radiation detector, comprising:
radiation detection element arrays in which a plurality of radiation detection elements detecting a radiation generated from a radiation source are arranged in a first direction and a second direction orthogonal to the first direction;
collimator plates that are arranged along the first direction on the radiation source side of the radiation detection element arrays to remove scattered radiations; and
collimator plate support members that have grooves supporting the collimator plate and are arranged along the second direction between the radiation detection elements;
wherein a width between radiation detection elements where the collimator plate support members are arranged is wider than a width between radiation detection elements where the collimator plate support members are not arranged.

2. The radiation detector according to claim 1, wherein there are even numbers of the collimator plate support members, and they are provided in symmetric positions on the basis of the central position in the first direction.

3. The radiation detector according to claim 1, wherein the radiation detection elements are composed of scintillator elements for generating a visible light when a radiation is incident as well as light detection elements for outputting an electrical signal when the visible light is incident, reflectors for reflecting the visible light are provided between the scintillator elements, and the collimator plate support members are composed of the same material as the reflectors.

4. An X-ray CT apparatus, comprising:

the radiation source; the radiation detector according to claim 1, that is disposed opposite to the radiation source to detect a radiation transmitted through an object; a rotating disk that is equipped with the radiation source and the radiation detector and rotating around the object; and image reconstruction device for reconstructing a tomographic image of the object based on a transmitted radiation amount detected by the radiation detector from multiple angles; and an image display device for displaying the tomographic image reconstructed by the image reconstruction device.

5. The X-ray CT apparatus according to claim 4, wherein the X-ray CT apparatus has a predetermined maximum slice thickness for image reconstruction, and wherein a position where collimator plate support members of the radiation detector are arranged is a joint position of the maximum slice thickness.

6. The radiation detector according to claim 1, wherein the collimator plate support members include an epoxy resin.

\* \* \* \* \*